United States Patent [19]

Lalezari

[11] 4,436,825
[45] Mar. 13, 1984

[54] PROCESS AND REAGENTS FOR ANTIBODY DETECTION INVOLVING ERYTHROCYTE AGGLUTINATION

[75] Inventor: Parviz Lalezari, Scarsdale, N.Y.

[73] Assignee: Montefiore Hospital and Medical Center, Inc., Bronx, N.Y.

[21] Appl. No.: 380,939

[22] Filed: May 21, 1982

Related U.S. Application Data

[63] Continuation of Ser. No. 144,447, Apr. 28, 1980, abandoned.

[51] Int. Cl.³ .......................................... G01N 33/54
[52] U.S. Cl. .................................... 436/520; 424/11; 436/17
[58] Field of Search ................ 436/520, 17; 424/11

[56] References Cited

PUBLICATIONS

Chemical Abstracts, 70:45715y (1969).
P. Lalezari, Transfusion, 8(6), 372–380, (1968).
R. R. A. Coombs et al., Brit. J. Exp. Path., 26, 255–266, (1945).
An-Fu Jiang et al., J. of Immunological Methods, 7, 103–108, (1975).

*Primary Examiner*—Sidney Marantz
*Attorney, Agent, or Firm*—Donald L. Barbeau

[57] ABSTRACT

A process for the detection of antibodies in a test sample is described. This process involves:
(a) preparing an essentially isotonic and low ionic strength suspension comprising said sample and erythrocytes in net negatively-charged form;
(b) maintaining said suspension for at least 30 seconds;
(c) combining said suspension with an amount of a solution of polymer effective for agglutination of said erythrocytes;
(d) separating the resultant agglutinates of polymer and erythrocytes from supernatant of said suspension;
(e) dispersing said agglutinates in a hypertonic salt solution having an essentially neutral pH; and
(f) monitoring the dispersed agglutinates for dissociation of erythrocytes.

This process permits rapid detection of antibodies with great ease. Their presence is indicated by persistence of the agglutinates in the dispersion. The antigen which reacts with antibody may be native to the erythrocytes, or may be unrelated to erythrocytes but artificially coupled to those cells. Quantitative analysis is likewise possible because their dissociation is inversely related to antibody concentration.

40 Claims, No Drawings

PROCESS AND REAGENTS FOR ANTIBODY DETECTION INVOLVING ERYTHROCYTE AGGLUTINATION

This application is a continuation of U.S. Ser. No. 144,447 filed on Apr. 28, 1980, abandoned.

BACKGROUND OF THE INVENTION

Numerous techniques for the detection of antibodies exist. These are utilized in many applications to determine the presence of any, or given, antibodies and to measure their concentration in a variety of fluids, most particularly blood. These techniques are particularly useful in the cross-matching of blood for transfusion.

The most commonly employed prior art procedures are based of the use of antiglobulin reagent. Representative procedures are described in an article by Coombs et al at Vol. 26, page 255 of the *Brit. J. Exp. Path* (1945). These procedures, however, have the drawbacks of being time-consuming and of inadequate sensitivity.

Another method is described in an article in *Transfusion*, Vol. 8, No. 6 November-December 1968 by P. Lalezari. That method utilizes an approach similar to the process of this invention. In common with other known techniques, however, that method has substantial drawbacks. It involves careful attention to proportions of ingredients and reagents as well as complicated equipment. Further, it too is time-consuming.

The disclosures of these articles are incorporated herein by reference. The drawbacks of these existing techniques pose substantial impediments to the need for fast and simple detection with acceptable accuracy. The need for improved detection techniques is therefore clear.

INTRODUCTION TO THE INVENTION

The process of this invention solves many of the drawbacks of known techniques for the detection of antibodies. It involves the steps of:
(a) preparing an essentially isotonic and low ionic strength suspension comprising said sample and erythrocytes is net negatively-charged form;
(b) maintaining said suspension for at least 30 seconds;
(c) combining said suspension with an amount of a solution of polymer effective for agglutination of said erythrocytes;
(d) separating the resultant agglutinates of polymer and erythrocytes from supernatant of said suspension;
(e) dispersing said agglutinates in a hypertonic salt solution having an essentially neutral pH; and
(f) monitoring the dispersed agglutinates for dissociation of erythrocytes.

This process may be completed in mere minutes with simple laboratory equipment. Moreover, it produces accurate results which are substantially independent of most variations in the amount or type of ingredients and reactants employed.

DESCRIPTION OF THE INVENTION

The present process is suitable for detection of antibodies in any, normally aqueous, sample. Most commonly, it is applied to a blood serum (including derivatives thereof). Erythrocytes must be added to the sample. The erythrocytes may first be washed, normally with isotonic salt solution. Desirably the sample contains from 0.1 to 1% more preferably 0.3 to 0.8%, suspended erythrocytes (or antigen coated erythrocytes) by total volume. These erythrocytes are normally obtained from a different source donor to ensure that they will accept any antibodies present in the sample. Erythrocytes may be obtained from the same donor as the serum if the presence of an autoantibody is being sought.

In the sample suspension, the erythrocytes should exhibit a net negative charge. This is the normal or native state of an erythrocyte. In this form, they will possess maximum sensitivity to subsequent agglutination. The negative charge is ensured by maintaining a pH of between about 6.0 and 6.6.

Maximum agglutination is also achieved in an essentially isotonic and low ionic strength suspension. The low ionic strength appears to sensitize the erythrocytes for acceptance of antibodies. Therefore a final salt concentration of from about 0.02 to 0.05, especially about 0.03, molar is preferred.

Although many additives may be employed to achieve these suspension conditions, addition of sugars—such as dextrose—are most convenient for increasing osmotic pressure. Virtually any salt may be used to increase ionic strength and simple dilution will reduce both of these conditions.

In a preferred embodiment, a special salt is employed in the suspension medium. This salt is disodium ethylenediamine tetra-acetate. Not only does it greatly facilitate sensitization of erythrocytes to antibody, but it additionally eases and/or accentuates other steps in the present process.

A preferred medium for combination with the test sample therefore comprises an aqueous solution comprising from 0.005 to 0.025% ethylenediamine tetra-acetate ion (optimally 0.01%) and from 4 to 8, desirably 5 percent of sugar such as dextrose or other mono-saccharide.

Once the suspension has been prepared, antibody-erythrocyte sensitization for subsequent steps is rapidly reached (if, that is, antibody is present in the test sample). The suspension need be maintained for a minimum of only about 30 seconds before addition of polymer in order to ensure the fidelity of the detection process.

Agglutination of the suspended erythrocytes is accomplished by addition of a solution of polymer. Many polymers effective for this purpose are either known or readily identifiable. These polymers include net positively-charged ones such as quaternary ammonium salts or negatively-charged ones such as carboxymethylcellulose. Preferred for this purpose is hexadimethrine bromide.

The amount of reactive polymer added to the suspension is not critical. Normally, however, sufficient polymer is employed to at least agglutinate all the erythrocytes. An excess is actually preferred to ensure accuracy in quantitative detections.

After addition, the polymer usually requires less than 30 seconds to completely perform its function. Thereafter, the polymer-erythrocyte agglutinates may be separated. This is most conveniently accomplished by centrifugation followed by decantation of the clear supernatant.

After separation, the agglutinates are dispersed, preferably under milk agitation, in a hypertonic salt solution having an essentially neutral pH. Again, their proportions in the dispersion medium are not critical, although a pH of from 6.8 to 7.5 is preferred. Within seconds, the existence or absence of antibodies becomes evident.

The constituents of the salt solution (dispersion) are also not critical, but may vary as previously described with respect to the suspension medium. In a preferred embodiment, however, the salt employed in the dispersion is a citrate (for example, a sodium, potassium, ammonium or like citrate). Such salts have been discovered to facilitate agglutinate dissociation where antibodies are not present. This both accelerates the process and facilitates monitoring by clarifying the detection endpoint.

A preferred dispersion medium for use in the present invention therefore comprises a hypertonic solution having a pH of from 6.8 to 7.5 and comprising from about 0.1 to 0.3 molar citrate ion. Normally it also contains a sugar, such as dextrose, or other mono-saccharide, from about 1.5 to 5, preferably about 2 percent by weight.

In the absence of antibodies, the agglutinates rapidly dissociate and reassume a suspension or colloidal form. In contrast, the presence of antibody is evidenced by its coupling effect on the erythrocytes. Therefore antibodies are revealed or detected by persistence of the agglutinates within the dispersion.

These results allow detection to occur through simple monitoring of the dispersed agglutinates. For example, visual monitoring (aided, if desired, by a microscope) allows rapid observation of the degree, if any, to which the agglutinate dissociates. Such dissociation occurs in inverse relationship to the concentration of antibody in the initial test sample.

This relationship also allows for precise quantitative measurement of antibody concentration. By use of either standardized conditions in the process or duplication utilizing control samples, accurate quantitative analysis is achieved.

The process of this invention is normally carried out under ambient (about 16° to 22° C.) conditions. This is not, however, necessary. Use of cold temperatures may be advantageous to permit separate detection of cold-reactive antibodies. These known antibodies preserve agglutination only at lower than ambient temperatures. Consequently, they may be detected only by chilling the agglutinates to from about 0° to 6° C. prior to dispersion and monitoring. Accordingly, this process also allows qualitative detection of antibodies which are cold versus ambient reactive.

Further qualitative analysis is possible in accordance with the process of this invention. The dissociated erythrocyte dispersion may be retested for certain antibodies which may not be detected by the agglutination. This is accomplished by addition of any oligo- or polyspecific antiglobulin reagent reacting with, for example, all IgG subclasses and the λ and κ chains common to immunoglobulins. Desirably, the reagent employed is inert to the common complement components of blood or serum.

Suitable, representative antiglobulin reagents are available commercially in varying degrees of specificity. Addition of such a reagent causes erythrocyte agglutination if such antibody is present. Consequently, this supplementary test readily increases the total accuracy of the present process by monitering for antibodies which might otherwise escape detection.

The process of this invention will be more fully described and better understood from the following examples.

EXAMPLE I

One-tenth ml (two drops) of a test serum sample was placed in a 12×75 mm glass tube followed by the addition of erythrocytes to give a concentration of about 0.5 percent. One ml of a low ionic aqueous diluent composed of 5% dextrose and 0.01% disodium ethylenediamine tetra-acetate was then added. The mixture was kept at room temperature in low ionic phase for one minute.

One-tenth ml (two drops) of a 0.05% aqueous solution of Polybrene (hexadimethrine bromide produced by Aldrich Chemical Company, Milwaukee, Wisc.) was added to the tube and mixed. Fifteen seconds later, the tube was centrifuged at 1000×g for ten seconds, and the cell-free supernatant fluid was decanted.

Polybrene-induced agglutination was reversed by adding 0.1 ml (two drops) of a solution of 60 ml 0.2 M trisodiumcitrate solution with 40 ml 5% dextrose to the tube under gentle agitation. Within ten seconds, the Polybrene-induced aggregates partially dissociated. This positive reaction was readily observed macroscopically. It confirmed the presence of antibody in the test serum.

EXAMPLE II

The process of Example I was repeated with a new test sample. Instead of performing all steps at ambient temperature, the agglutinates remaining after decantation were chilled in an ice bath for one minute.

Upon subsequent dispersion in the solution, the agglutinates immediately dissociated completely. This evidenced an absence of antibodies, including cold reactive ones.

EXAMPLE III

The dispersion of dissociated erythrocytes of Example II was washed twice with a 0.9% sodium chloride solution which also contained 0.01 M trisodium citrate solution. The washed cells were then combined with two drops of aqueous solution of anti-globulin reagent (Lot. No. 056-53, Dade, Division of American Hospital Supply Corporation). The test tube was then centrifuged for 10 seconds and the erythrocytes were examined for agglutination. No agglutination was observed, thus indicating the absence of antibodies.

In the foregoing Examples, monitoring was performed simply through visual inspection of macroscopic agglutinate particles. They therefore constituted only negative-positive detection tests. More accurate and quantitative results may be obtained by careful microscopic monitoring involving detection of degree of erythrocyte dissociation. Similar results may be obtained by other techniques including, for example, photometric analysis of the dispersion medium shortly after agglutinate addition. In this instance, analysis for colloidal, individual erythrocytes allows precise measurement of degree of dissociation.

For these quantitative processes of the present invention, control samples are often run in tandem with the test sample. This ensures accuracy of detection measurement. Such controls may either possess no, or a predetermined amount of, antibody as per conventional analytic technique.

In addition to the various reagent constituents previously mentioned, others may be present. These constituents include bactericides, such as sodium azide, to avoid contamination; sugars, such as dextrose, to provide nutrients and sufficient osmotic pressure to ensure normalacy of the erythrocytes; and the like for similar known or apparent purposes.

It is to be understood that these changes may be made in the following exemplary embodiments in the light of the above teachings. Additional modifications and/or variations may also be made without departing from the scope and spirit of the invention which therefore shall be measured by the claims which follow.

What is claimed is:

1. A process for the detection of antibodies in a test sample comprising:
    (a) preparing an essentially isotonic and low ionic strength suspension comprising said sample, a sensitization effective amount of ethylenediamine tetra-acetate, and erythrocytes in net negatively-charged form;
    (b) maintaining said suspension for at least 30 seconds;
    (c) combining said suspension with an amount of a solution of polymer effective for agglutination of said erythrocytes;
    (d) separating the resultant agglutinates of polymer and erythrocytes from supernatant of said suspension;
    (d) dispersing said agglutinates without bound antibody in a hypertonic salt solution having an essentially neutral pH; and
    (f) monitoring the resuspended agglutinates for the presence or absence of antibody.

2. The process of claim 1 wherein the dispersed agglutinates without bound antibody are monitored for dissociation.

3. The process of claim 1 wherein the undispersed agglutinates with bound antibody are monitored.

4. A process for the detection of antibodies in a test sample comprising:
    (a) preparing an essentially isotonic and low ionic strength suspension comprising said sample and erythrocytes in net negatively-charged form;
    (b) maintaining said suspension for at least 30 seconds;
    (c) combining said suspension with an amount of a solution of polymer effective for agglutination of said erythrocytes;
    (d) separating the resulting agglutinates of polymer and erythrocytes from supernatant of said suspension;
    (e) dispersing said agglutinates without bound antibody in a hypertonic salt solution having a pH of from 6.8 to 7.5;
    (f) monitoring the resuspended agglutinates for the presence or absence of antibody.

5. The process of claim 4 wherein the dispersed agglutinates without bound antibody are monitored for dissociation.

6. The process of claim 4 wherein the undispersed agglutinates with bound antibody are monitored.

7. The process of claim 4 wherin the low ionic strength suspension further comprises ethylenediamine tetra-acetate.

8. The process of claim 4 wherein the low ionic strength suspension further comprises a sensitization effective amount of ethylenediamine tetra-acetate having a pH of from about 6.0 to 6.6, and from 3.3 to 6.7% sugar by weight.

9. The process of claim 4 wherein the hypertonic salt solution has a pH of from 6.8 to 7.5 and further comprises an aqueous solution of from about 0.1 to 0.3 molar citrate salt and from about 1.5 to 5% sugar by weight.

10. The process of claim 1, 2, 3, 4, 5, or 6, wherein the test sample is selected from the group consisting of blood and blood serum.

11. The process of claim 1, 2, 3, 4, 5, or 6, wherein the suspension comprises from 0.1 to 1% erythrocytes by volume.

12. The process of claim 1, 2, 3, 4, 5, or 6, wherein the polymer is a negatively-charged polymer.

13. The process of claim 1, 2, 3, 4, 5, or 6, wherein the polymer is a positively-charged polymer.

14. The process of claim 13, wherein the polymer is a quaternary ammonium salt.

15. The process of claim 13, wherein the polymer is hexadimethrine bromide.

16. The process of claim 1, 2, or 3, wherein the suspension has a pH of between about 6.0 and 6.6.

17. The process of claim 1, 2, or 3, wherein the agglutinates are at a temperature of from about 16° to 22° C. when dispersed.

18. The process of claim 1, 2, or 3, wherein the agglutinates are at a temperature of from about 0° to 6° C. when dispersed.

19. The process of claim 4, 5, 6, or 7 wherein antiglobulin reagent is added to the agglutinates to monitor for antibody.

20. The process of claim 1, 2, 3, 4, 5, 6, or 7 wherein the antigen is native to the erythrocytes.

21. The process of claim 1, 2, 3, 4, 5, 6, or 7 wherein the antigen is artificially coupled to the erythrocytes.

22. A reagent for use in the detection of antibodies comprising a medium having a sensitization effective pH, and containing a sensitization effective amount of ethylenediamine tetra-acetate and from 4 to 8% sugar by weight.

23. The reagent of claim 22, which additionally comprises erythrocytes.

24. The reagent of claim 22, which additionally comprises from 0.02 to 0.2% erythrocytes by volume.

25. The reagent of claim 22, wherein the total salt concentration is from about 0.005 to 0.025 molar.

26. The reagent of claim 25, wherein the sugar is a mono-saccharide.

27. The reagent of claim 26, which additionally comprises erythrocytes.

28. The reagent of claim 27, wherein said reagent is at a temperature of from about 16° to 22° C.

29. The reagent of claim 27, wherein said reagent is at a temperature of from about 0° to 6° C.

30. The reagent of claim 27, which additionally comprises from 0.02 to 0.2% erythrocytes.

31. A reagent for use in the detection of antibodies comprising a medium having a pH of from 6.8 to 7.5 and containing from 0.1 to 0.3 molar citrate salt and from about 1.5 to 5% sugar by weight.

32. The reagent of claim 31, wherein said reagent is at a temperature of from about 16° to 22° C.

33. The reagent of claim 31, wherein said reagent is at a temperature offrom about 0° to 6° C.

34. The reagent of claim 31, wherein the sugar is a mono-saccharide.

35. The reagent of claim 34, wherein the cation of the citrate salt is selected from the group consisting of sodium, potassium and ammonium.

36. A process for the detection of antibodies in a test sample comprising;
    (a) preparing an essentially isotonic and low ionic strength suspension comprising said sample and erythrocytes in net negatively-charged form;

(b) maintaining said suspension for at least 30 seconds;
(c) combining said suspension with an amount of a solution of polymer effective for agglutination of said erythrocytes;
(d) separating the resultant agglutinates of polymer and erythrocytes from supernatant of said suspension;
(e) dispersing said agglutinates in a hypertonic salt solution having an essentially neutral pH;
(f) monitoring the dispersed agglutinates for dissociation of erythrocytes; and
(g) retesting of dissociated erythrocytes for antibodies which are not detected by steps (a) through (f) by adding oligo- or poly-specific antiglobulin reagent to monitor for previously undetected antibodies.

37. A process for the detection of antibodies in a test sample comprising:
(a) preparing an essentially isotonic and low ionic strength suspension comprising said sample, an aqueous solution of a sensitization effective amount of ethylenediamine tetra-acetate having a pH of from about 6.0 to 6.6, from 4 to 8% sugar by weight, and erythrocytes in net negatively-charged form;
(b) maintaining said suspension for at least 30 seconds;
(c) combining said suspension with an amount of a solution of polymer effective for agglutination of said erythrocytes;
(d) separating the resultant agglutinates of polymer and erythrocytes from supernatant of said suspension;
(e) dispersing said agglutinates in a hypertonic salt solution having an essentially neutral pH; and
(f) monitoring the dispersed agglutinates for dissociation of erythrocytes.

38. A process for the detection of antibodies in a test sample comprising:
(a) preparing an essentially isotonic and low ionic strength suspension comprising said sample, a sensitization effective amount of ethylenediamine tetra-acetate, and erythrocytes in net negatively-charged form;
(b) maintaining said suspension for at least 30 seconds;
(c) combining said suspension with an amount of a solution of polymer effective for agglutination of said erythrocytes;
(d) separating the resultant agglutinates of polymer and erythrocytes from supernatant of said suspension;
(e) dispersing said agglutinates in a hypertonic salt solution having a pH of from 6.8 to 7.5; and
(f) monitoring the dispersed agglutinates for the presence or absence of antibody.

39. A process for the detection of antibodies in a test sample comprising:
(a) preparing an essentially isotonic and low ionic strength suspension comprising said sample and erythrocytes in net negatively-charged form;
(b) maintaining said suspension for at least 30 seconds;
(c) combining said suspension with an amount of a solution of polymer effective for agglutination of said erythrocytes;
(d) separating the resultant agglutinates of polymer and erythrocytes from supernatant of said suspension;
(e) dispersing said agglutinates in a hypertonic salt solution having an essentially neutral pH;
(f) monitoring the resuspended agglutinates for the presence of antibody;
(g) retesting of dissociated erythrocytes for antibodies which are not detected by steps (a) through (f) by adding oligo- or poly-specific antiglobulin reagent to monitor for previously undetected antibodies.

40. A reagent for use in the detection of antibodies comprising a medium having a pH of from 6.0 to 6.6 and containing a sensitization effective amount of ethylenediamine tetra-acetate and from 4 to 8% sugar by weight.

* * * * *